United States Patent
Mangold et al.

(10) Patent No.: US 12,377,222 B2
(45) Date of Patent: Aug. 5, 2025

(54) RECEPTACLE FOR PHARMACEUTICAL PACKAGING HAVING A GRADUATED LUBRICANT LAYER

(71) Applicant: SCHOTT Pharma AG & Co. KGaA, Mainz (DE)

(72) Inventors: Stephanie Mangold, Schornsheim (DE); Raymond Moser, Engelburg (CH)

(73) Assignee: SCHOTT Pharma AG & Co. KGaA, Mainz (DE)

( * ) Notice: Subject to any disclaimer, the term of this patent is extended or adjusted under 35 U.S.C. 154(b) by 1017 days.

(21) Appl. No.: 17/100,021

(22) Filed: Nov. 20, 2020

(65) Prior Publication Data
US 2021/0154409 A1    May 27, 2021

(30) Foreign Application Priority Data
Nov. 21, 2019   (EP) ..................................... 19210762
Mar. 6, 2020    (EP) ..................................... 20161540

(51) Int. Cl.
*A61M 5/31*    (2006.01)
*C10M 107/50*  (2006.01)
*C10N 40/00*   (2006.01)

(52) U.S. Cl.
CPC ........ *A61M 5/3129* (2013.01); *C10M 107/50* (2013.01); *A61M 2005/3131* (2013.01); *C10M 2229/025* (2013.01); *C10N 2040/50* (2020.05)

(58) Field of Classification Search
CPC ........ A61M 5/3129; A61M 2005/3131; A61M 2005/31506; A61M 2205/0222; A61M 2205/0238; C10N 2040/50; C10M 107/50; A61L 29/085
See application file for complete search history.

(56) References Cited

U.S. PATENT DOCUMENTS

| | | | | |
|---|---|---|---|---|
| 4,767,414 A * | 8/1988 | Williams | ................ | A61M 5/31 604/230 |
| 6,213,985 B1 * | 4/2001 | Niedospial, Jr. | ..... | A61M 5/3129 604/218 |
| 6,283,946 B1 * | 9/2001 | Fischer | ............. | B05C 17/00593 604/218 |

(Continued)

FOREIGN PATENT DOCUMENTS

| | | |
|---|---|---|
| EP | 0 920 879 B1 | 4/2003 |
| JP | 5138917 A | 11/2012 |

(Continued)

OTHER PUBLICATIONS

European Search Report dated Feb. 13, 2020 for European Patent Application No. 19210764 (5 pages).

(Continued)

*Primary Examiner* — Michael J Tsai
*Assistant Examiner* — Justin L Zamory
(74) *Attorney, Agent, or Firm* — TAYLOR & EDELSTEIN, PC

(57) ABSTRACT

A receptacle for pharmaceutical packaging includes: an elongate barrel section; a side wall extending over the elongate barrel section, the side wall having an inner surface bordering an interior, the interior having a diameter; and a layer of a lubricant located on at least a part of the inner surface. A thickness of the layer of lubricant is graduated.

20 Claims, 10 Drawing Sheets

(56) References Cited

U.S. PATENT DOCUMENTS

| | | | |
|---|---|---|---|
| 10,066,182 B2 * | 9/2018 | Santucci-Aribert | ... B05D 3/068 |
| 2001/0004466 A1 * | 6/2001 | Heinz | ... A61L 29/085 |
| | | | 427/2.1 |
| 2007/0299402 A1 | 12/2007 | Ishii et al. | |
| 2010/0305513 A1 | 12/2010 | Araki et al. | |
| 2017/0182252 A1 | 6/2017 | Hamel et al. | |
| 2018/0015225 A1 | 1/2018 | Vogt | |
| 2021/0154409 A1 | 5/2021 | Mangold et al. | |

FOREIGN PATENT DOCUMENTS

| | | | |
|---|---|---|---|
| JP | 2017-78003 A | 4/2017 | |
| WO | 2013099447 A1 | 7/2013 | |
| WO | 2014/190225 A1 | 11/2014 | |

OTHER PUBLICATIONS

Communication pursuant to Article 94(3) EPC for European Patent Application No. 19210764 (4 pages).
European Search Report dated Sep. 17, 2020 for European Patent Application No. 20 16 1539 (4 pages).
European Search Report dated Feb. 7, 2020 for European Patent Application No. 19210762 (4 pages).

* cited by examiner

RECEPTACLE FOR PHARMACEUTICAL PACKAGING HAVING A GRADUATED LUBRICANT LAYER

CROSS REFERENCE TO RELATED APPLICATIONS

This application claims priority to European Patent Application No. 19210762.1 filed on Nov. 21, 2019 and European Patent Application No. 20161540.8 filed on Mar. 6, 2020, which are both incorporated in their entirety herein by reference.

BACKGROUND OF THE INVENTION

1. Field of the Invention

The invention generally relates to a receptacle for pharmaceutical packaging having a graduated layer of lubricant. In particular, the invention relates to a receptacle; a kit comprising a receptacle and a charge; an assembly comprising a receptacle, a charge and a liquid pharmaceutical composition; a process for the preparation of a receptacle and a use of a lubricant layer of graduated thickness.

2. Description of the Related Art

Pharmaceutical material can be provided in a number of forms and contained in a variety of different containers. In the case of a liquid pharmaceutical material, some common examples are ampules, vials, cartridges and syringes. One widely used format employs a sliding plunger within a container for ejecting a liquid out of an aperture. One approach is to provide a lubricating layer on the inside of the container to facilitate sliding movement of the plunger.

U.S. Pat. No. 4,767,414 A describes plasma activation of an inner surface prior to application of a layer of silicone lubricant.

European Patent No. EP 0920879 B1 describes a recipe for a silicone-based mixture comprising reactive components and unreactive components.

There persists a need for improved approaches to lubrication of pharmaceutical containers, in particular for delivering multiple separate doses from a single container.

SUMMARY OF THE INVENTION

In some exemplary embodiments provided according to the present invention, a receptacle for pharmaceutical packaging has a graduated layer of lubricant.

In some exemplary embodiments provided according to the present invention, a receptacle for pharmaceutical packaging includes: an elongate barrel section, the elongate barrel section having a direction of elongate extension and an axis in the direction of elongate extension, an axial position p is determined along the axis, the elongate barrel section extends from an axial position pA to an axial position pB, and an elongate barrel section length LB is a distance between pA and pB; a side wall extending over the elongate barrel section, the side wall having an inner surface bordering an interior, the interior having a diameter; and a layer of a lubricant located on at least a part of the inner surface. At a given axial position p on the axis between pA and pB, a thickness of the side wall, a thickness of the layer, and the diameter of the interior are each determined as an angular mean in a cross-sectional plane perpendicular to the axis at the axial position p. A portion X of the axis extends from an axial position p1 to an axial position p2 such that the following criteria are satisfied: i. both p1 and p2 lie between pA and pB, ii. a portion length LX is a distance between p1 and p2, iii. LX is at least a quarter of LB, iv. the layer extends over the entire portion X, and v. a thickness t1 of the layer at p1 is less than a thickness t2 of the layer at p2. At least one criteria is satisfied and is selected from the group consisting of: the length LB is in a range from 3 cm to 20 cm; a mean value of the diameter of the interior determined over a range pA to pB is in a range from 0.4 cm to 4 cm; a mean thickness of the sidewall determined over the range pA to pB is in a range from 0.3 mm to 4 mm; and a volume of the interior is in a range from 0.1 ml to 150 ml.

In some exemplary embodiments provided according to the present invention, a kit includes a receptacle and a charge. The receptacle includes: an elongate barrel section, the elongate barrel section having a direction of elongate extension and an axis in the direction of elongate extension, an axial position p is determined along the axis, the elongate barrel section extends from an axial position pA to an axial position pB, and an elongate barrel section length LB is a distance between pA and pB; a side wall extending over the elongate barrel section, the side wall having an inner surface bordering an interior, the interior having a diameter; and a layer of a lubricant located on at least a part of the inner surface. At a given axial position p on the axis between pA and pB, a thickness of the side wall, a thickness of the layer, and the diameter of the interior are each determined as an angular mean in a cross-sectional plane perpendicular to the axis at the axial position p. A portion X of the axis extends from an axial position p1 to an axial position p2 such that the following criteria are satisfied: i. both p1 and p2 lie between pA and pB, ii. a portion length LX is a distance between p1 and p2, iii. LX is at least a quarter of LB, iv. the layer extends over the entire portion X, and v. a thickness t1 of the layer at p1 is less than a thickness t2 of the layer at p2. At least one criteria is satisfied and is selected from the group consisting of: the length LB is in a range from 3 cm to 20 cm; a mean value of the diameter of the interior determined over a range pA to pB is in a range from 0.4 cm to 4 cm; a mean thickness of the sidewall determined over the range pA to pB is in a range from 0.3 mm to 4 mm; and a volume of the interior is in a range from 0.1 ml to 150 ml. The charge is adapted and arranged to be positioned in the interior such that: i. the charge seals a cross section of the interior between the inner surface of the side wall and another inner surface of a second side wall; ii. the charge has a front end at an axial position closest to pB at which the charge contacts the layer or the inner surface; iii. the charge has a back end at an axial position closest to pA at which the charge contacts the layer or the inner surface; iv. a length of the charge LC is a distance between the front end and the back end; v. the charge has a charge axial position, being the axial position of the front end; and vi. the charge is movable in a direction parallel to the axis with a stiction s, the stiction s being a function of the charge axial position.

In some exemplary embodiments provided according to the present invention, an assembly includes a receptacle and a charge. The receptacle includes: an elongate barrel section, the elongate barrel section having a direction of elongate extension and an axis in the direction of elongate extension, an axial position p is determined along the axis, the elongate barrel section extends from an axial position pA to an axial position pB, and an elongate barrel section length LB is a distance between pA and pB; a side wall extending over the elongate barrel section, the side wall having an inner surface bordering an interior, the interior having a diameter; and a layer of a lubricant located on at least a part of the inner surface. At a given axial position p on the axis between pA and pB, a thickness of the side wall, a thickness of the layer, and the diameter of the interior are each determined as an angular mean in a cross-sectional plane perpendicular to the axis at the axial position p. A portion X of the axis extends from an axial position p1 to an axial position p2 such that the following criteria are satisfied: i. both p1 and p2 lie between pA and pB, ii. a portion length LX is a distance between p1 and p2, iii. LX is at least a quarter of LB, iv. the layer extends over the entire portion X, and v. a thickness t1 of the layer at p1 is less than a thickness t2 of the layer at p2. At least one criteria is satisfied and is selected from the group consisting of: the length LB is in a range from 3 cm to 20 cm; a mean value of the diameter of the interior determined over a range pA to pB is in a range from 0.4 cm to 4 cm; a mean thickness of the sidewall determined over the range pA to pB is in a range from 0.3 mm to 4 mm; and a volume of the interior is in a range from 0.1 ml to 150 ml. The receptacle has an aperture. The charge is positioned in the interior sealing a cross section of the interior. The interior contains a liquid pharmaceutical composition, located between the sealed cross section and the aperture, and the assembly is adapted and arranged for the liquid pharmaceutical composition to be ejected through the aperture by movement of the charge in a direction parallel to the axis.

Exemplary embodiments disclosed herein provide an improved receptacle for pharmaceutical packaging, in particular for multi-dose delivery.

Exemplary embodiments disclosed herein provide an improved kit comprising a receptacle and a charge, in particular for multi-dose delivery.

Exemplary embodiments disclosed herein provide an improved process for preparing a receptacle for pharmaceutical packaging, in particular for multi-dose delivery.

Exemplary embodiments disclosed herein provide an improved assembly including a receptacle, a charge and a liquid pharmaceutical composition, in particular for multi-dose delivery.

Exemplary embodiments disclosed herein provide a receptacle for pharmaceutical packaging having improved stiction properties, in particular for multi-dose delivery.

Exemplary embodiments disclosed herein provide a kit having improved stiction properties, in particular for multi-dose delivery.

Exemplary embodiments disclosed herein provide a process for preparing a receptacle for pharmaceutical packaging providing improved stiction properties, in particular for multi-dose delivery.

Exemplary embodiments disclosed herein provide an assembly having improved stiction properties, in particular for multi-dose delivery.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 1:
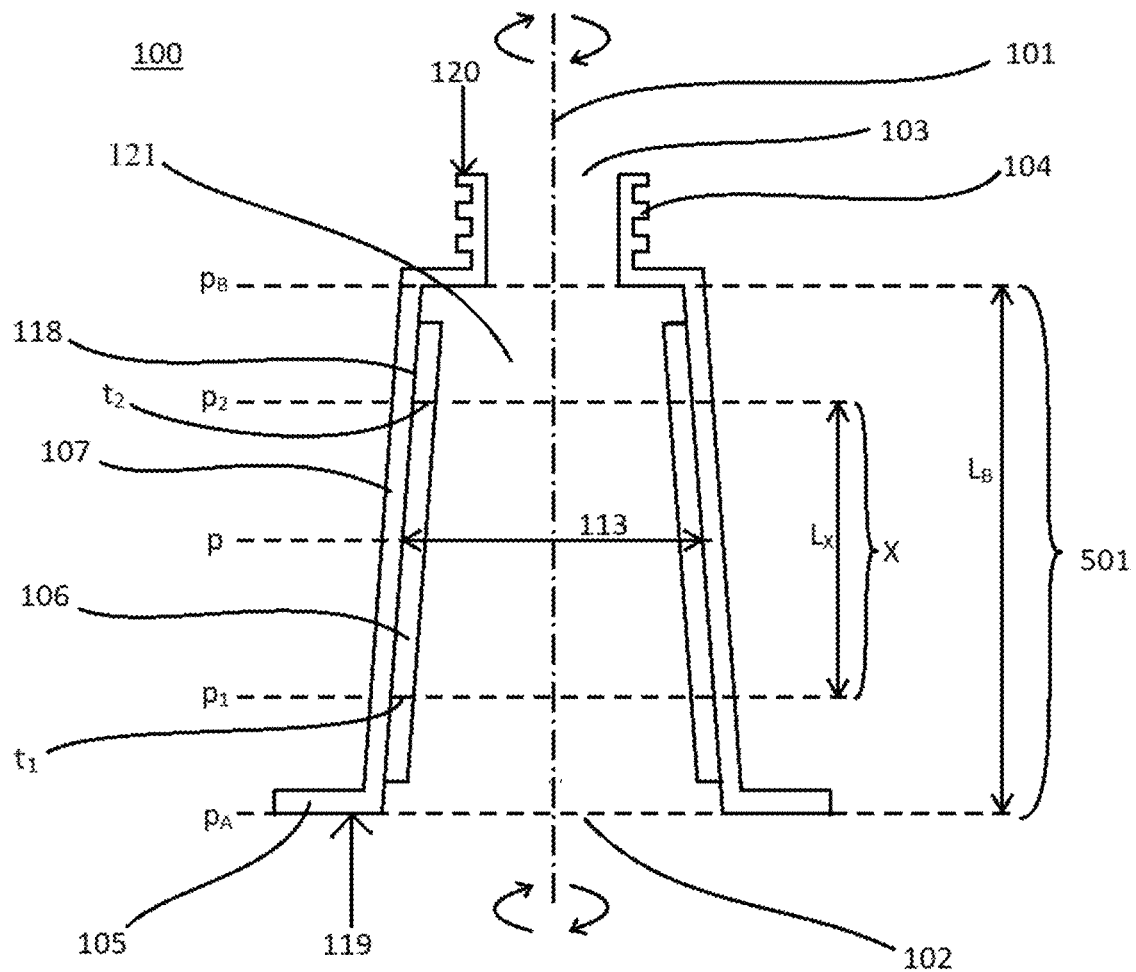
FIG. 1 illustrates a cross-sectional view of a receptacle with a layer of lubricant on an inner surface of a side wall.

The following embodiments represent exemplary arrangements provided according to the present invention.

In some exemplary embodiments provided according to the present invention, a receptacle for pharmaceutical packaging has an elongate barrel section, wherein:
  a. the elongate barrel section has a direction of elongate extension and an axis in the direction of elongate extension;
  b. an axial position p is determined along the axis;
  c. the elongate barrel section extends from an axial position pA to an axial position pB;
  d. an elongate barrel section length LB is the distance between pA and pB;
  e. the receptacle has a side wall extending over the elongate barrel section, the side wall having an inner surface bordering an interior, the interior having a diameter;
  f. a layer of a lubricant is located on at least a part of the inner surface;
  g. at a given axial position p on the axis between pA and pB, the following:
    i. the thickness of the side wall,
    ii. the thickness of the layer, and
    iii. the diameter of the interior,
    are each determined as an angular mean in a cross-sectional plane perpendicular to the axis at the axial position p;
  h. a portion X of the axis extends from an axial position p1 to an axial position p2
    such that the following criteria are satisfied:
    i. both p1 and p2 lie between pA and pB,
    ii. a portion length LX is the distance between p1 and p2,
    iii. LX is at least a quarter of LB, preferably at least a half of LB, more preferably at least 80% of LB, most preferably at least 90% of LB,
    iv. the layer extends over the entire portion X, and
    v. a thickness t1 of the layer at p1 is less than a thickness t2 of the layer at p2;
  i. one or more receptacle criteria selected from the following are satisfied:
    i. The length LB is in the range from 3 to 20 cm, such as in the range from 4 to 15 cm, in the range from 5 to 12 cm, or in the range from 6 to 8 cm;
    ii. The mean value of the diameter of the interior determined over the range pA to pB is in the range from 0.4 to 4 cm, such as in the range from 0.6 to 3 cm, in the range from 0.8 to 2.5 cm, or in the range from 1 to 2 cm;

iii. The mean thickness of the sidewall determined over the range pA to pB is in the range from 0.3 to 4 mm, such as in the range from 0.7 to 3 mm, in the range from 1.1 to 2 mm, or in the range from 1.4 to 1.8 mm; and iv. The volume of the interior is in the range from 0.1 to 150 ml, such as in the range from 0.5 to 50 ml, in the range from 1 to 25 ml, in the range from 2 to 10 ml, or in the range from 3 to 5 ml.

In some embodiments, the following combinations of the receptacle criteria i. to iv. are fulfilled: i., ii., iii., iv., i.+ii., i.+iii., i.+iv., ii.+iii., ii.+iv., iii.+iv., i.+ii.+iii., i.+ii.+iv., i.+iii.+iv., ii.+iii.+iv & i.+ii.+iii.+iv.

In some embodiments, the ratio of the thicknesses t1:t2 is in the range from 1:1.1 to 1:100, such as in the range from 1:5 to 1:90, in the range from 1:10 to 1:80, or in the range from 1:15 to 1:70.

In some embodiments, the lubricant comprises one or more silicone oils. The lubricant may comprise in total at least 5 wt. %, such as at least 15 wt. % or at least 25 wt. %, of one or more silicone oils, based on the total weight of the lubricant of the layer.

In some embodiments, the one or more silicone oils are at least partially contained in a matrix that is bound to the inner surface.

In some embodiments, the matrix is a polymer, such as a crosslinked polymer.

In some embodiments, the polymer comprises SiO-containing repeating units. An exemplary polymer is a polysiloxane, such as a crosslinked polysiloxane.

In some embodiments, the interior is cylindrical or truncated conical over the elongate barrel section. An exemplary truncated cone has a cone aperture in the range from 0.04° to 0.4°, such as in the range from 0.08° to 0.25° or in the range from 0.1° to 0.2°.

In some embodiments, the receptacle includes a first aperture at a first end and a second aperture at a second end. The first aperture may have a greater area than the second aperture, such as at least 50% greater, at least 100% greater, or at least 200% greater, based on the surface area of the second aperture. In some embodiments, the receptacle includes a first aperture at a first end and a dead end at a second end.

In some embodiments, the internal diameter at p1 is d1 and the internal diameter at p2 is d2 and d1 is greater than d2. d1 may be at least 0.05% greater than d2, such as at least 0.1%, or at least 0.2%, based on the diameter d2. d1 may be up to 5% greater than d2, such as up to 4% or up to 3%, based on the diameter d2.

In some embodiments, the receptacle includes an aperture and an attachment element at the aperture. In some embodiments, an attachment element is at an end, such as at a second end. An exemplary attachment element is adapted and arranged for attaching a needle and/or a tube. Some exemplary attachment elements are a screw thread, a latch, a Luer fitting and a bayonet-style fitting.

In some embodiments, the layer has a minimum thickness tmin determined in the portion X of at least 60 nm, such as at least 90 nm, at least 100 nm, or at least 110 nm.

In some embodiments, a kit includes as kit parts:
a. the previously described receptacle, and
b. a charge.

The charge is adapted and arranged to be positioned in the interior such that:
i. the charge seals a cross section of the interior between the inner surfaces of the side walls;
ii. the charge has a front end at the axial position closest to pB at which the charge contacts the layer or the inner surface;
iii. the charge has a back end at the axial position closest to pA at which the charge contacts the layer or the inner surface;
iv. a length of the charge LC is the distance between the front end and the back end;
v. the charge has a charge axial position, being the axial position of the front end; and
vi. the charge is movable in a direction parallel to the axis with a stiction s, s being a function of the charge axial position.

An exemplary charge comprises an elastomeric material.

In some embodiments, for charge axial positions in the range from p1+LC to p2, the stiction s has a maximum value smax, a minimum value smin and the value of smin/smax is 40 or more, such as 50% or more, 60% or more, 65% or more, 70% or more, 75% or more, or 80% or more.

In some embodiments, the stiction at charge axial position p2 is equal to or less than the stiction at charge axial position p1+LC. In some embodiments, the stiction at charge axial position p2 is less than the stiction at charge axial position p1+LC by at least 5%, such as at least 10%, at least 15%, or at least 20%, based on the stiction at charge axial position p1+LC.

In some embodiments, an assembly includes the previously described receptacle and a charge, wherein:
a. the receptacle has an aperture;
b. the charge is positioned in the interior sealing a cross section of the interior;
c. the interior contains a liquid pharmaceutical composition, located between the sealed cross section and the aperture; and
d. the assembly is adapted and arranged for the liquid pharmaceutical composition to be ejected through the aperture by movement of the charge in a direction parallel to the axis.

In some embodiments, a process for preparing a previously described receptacle, a previously described kit, or a previously described assembly is provided. The process includes a process step of applying the layer of lubricant by spreading with a spreading tool.

In some embodiments, a use of a layer of lubricant of graduated thickness for improving uniformity of stiction in a pharmaceutical receptacle is provided.

Diameters, Layer Thicknesses and Roughness

The axis of the receptacle is used to determine axial position. At a given axial position, the side wall is a perimeter having a thickness lying in a cross-sectional plane perpendicular to the axis, likewise for the lubricant layer. Internal diameter, thickness of the lubricant layer, thickness of the side wall and surface roughness at a given point along the axis may be mean values determined around a perimeter. A mean around a perimeter is an angular mean. An angular mean may be determined by measuring at 8 points around the perimeter, the 8 points being separated by equal angles.

Monotonic Parameters

Herein, the term "monotonic", when applied to a variable dependent on p, may ignore sharp variations in the function with small changes in p, otherwise known as roughness. Monotonicity for a parameter Y over the portion X may be determined as follows:

the portion X is split into n sections of equal length: M1 to Mn;

M1 to Mn are ordered, with M1 starting at p1 and Mn finishing at p2;

the mean values of Y over the sections M1 to Mn are Y1 to Yn respectively;

for a monotonic increase, each mean value of Y through the series Y2 to Yn is greater than the preceding mean value of Y: Y1 to Yn−1 respectively;

for a monotonic decrease, each mean value of Y through the series Y2 to Yn is less than the preceding mean value of Y: Y1 to Yn−1 respectively;

n is an integer of 2 or more. Exemplary values for n are 5, 10, 15 and 20.

Receptacle

An exemplary receptacle is adapted and arranged to contain a pharmaceutical liquid. Some exemplary receptacles are syringes, syringe barrels, cartridges, dead-end containers and vials.

An exemplary receptacle has one or more apertures. An aperture may be located at an end of the receptacle. In some embodiments, the receptacle has one aperture. In other embodiments, the receptacle has two apertures.

The receptacle may have two ends, a first end and a second end.

An exemplary receptacle has a first aperture at a first end. One type of exemplary receptacle has a second aperture at a second end. Another type of exemplary receptacle has a dead end at a second end.

Elongate Barrel Section

The receptacle has an elongate barrel section. The elongate barrel section denominates a section of the receptacle. The receptacle may have further sections outside of the elongate barrel section. Another term for an elongate barrel section is a tube section. An exemplary elongate barrel section is tubular.

Exemplary embodiments of the elongate barrel section and the axis are described herein in mathematical terms, for example as axes of symmetry, rotation or revolution, surfaces and solids of revolution and shapes such as cylinders and truncated cones. These embodiments are to be understood as allowing some variation from these precise mathematical concepts. Suitable variations from the mathematic concepts are those which do not inhibit the receptacle from functioning as a plunger system in cooperation with a charge.

The elongate barrel section has an axis. The axis may be an axis of rotation for the elongate barrel section. The axis may be an axis of revolution for the elongate barrel section. The side wall may be a solid of revolution about the axis. The inner surface may be a surface of revolution about the axis. The layer may be a solid of revolution about the axis.

The axis defines an axial position p. The axial position p is an axial position along the axis. As used herein, the symbol p denotes an axial position in general terms and specific axial positions are denoted by the letter p with a subscript.

An axial position p along the axis is used as a parameter to describe the locations of points or cross-sections along the elongate barrel section, for example on the side wall. The axial position of a point not on the axis is found by projecting the point onto the axis by a displacement vector perpendicular to the axis. A cross section is a plane perpendicular to the axis. The axial position of a cross section is found at the point where the cross section meets the axis.

The elongate barrel section extends from an axial position pA to an axial position pB. The elongate barrel section is contained by a cross section at pA and a cross section at pB.

In some embodiments, the receptacle has a first end and a second end, the receptacle is adapted and arranged for ejecting a liquid pharmaceutical composition from the second end, and pB is closer to the second end than is pA.

In some embodiments, the receptacle has a first end and a second end, the first end is a dead end with no aperture, the second end is an open end with an aperture, and pB is closer to the second end than is pA.

The receptacle has a side wall extending over the elongate barrel section. The side wall has an inner surface. The inner surface borders an interior. Exemplary shapes for the side wall are a hollow cylinder, a hollow prism and a hollow truncated cone. An exemplary hollow truncated cone has a diameter which decreases from pA to pB. Exemplary shapes for the interior are a cylinder, a prism and a truncated cone. An exemplary truncated cone has a diameter which decreases from pA to pB.

The inner surface may be smooth or may have some roughness.

The thickness of the side wall may be measured as a difference in radial distance from the axis of the inner surface and an outer surface of the side wall.

The thickness of the layer may be measured as a difference in radial distance from the axis of an inner surface of the layer and the inner surface of the side wall.

Exemplary materials for the side wall are polymers and glasses.

In some embodiments, the side wall comprises a polymer, such as being made of a polymer. The polymer may be one or both selected from the group consisting of: one or more cyclic olefin copolymers and one or more cyclic olefin polymers. In some embodiments, the polymer is at least 30 wt. % of the side wall, such as at least 50 wt. %, at least 80 wt. %, or about 100 wt. %.

In some embodiments, the side wall comprises a glass, such as being made of a glass. An exemplary glass in this context comprises one or more elements selected from the group consisting of: silicon, boron, and aluminum. One exemplary glass comprises boron and silicon. One exemplary glass is a borosilicate glass. One exemplary glass comprises aluminum and silicon. One exemplary glass is an aluminosilicate glass. In some embodiments, the glass is at least 30 wt. % of the side wall, such as at least 50 wt. %, at least 80 wt. %, or about 100 wt. %.

Lubricant Layer

The layer of lubricant is located on the inner surface of the side wall. The lubricant layer may extend over the entire elongate barrel section or just a part of it. The lubricant layer extends over the entire portion X.

An exemplary lubricant is a silicone-based lubricant.

An exemplary lubricant comprises one or more polysiloxanes.

An exemplary lubricant comprises one or more silicone oils, with a total content of silicone oils in the range from 10 to 50 wt. %, such as in the range from 20 to 40 wt. % or in the range from 25 to 35 wt. %, based on the total weight of the lubricant. An exemplary silicone oil is a poly dimethyl silicone.

An exemplary lubricant comprises a crosslinked polysiloxane matrix, with a total content of crosslinked polysiloxane matrix in the range from 50 to 90 wt. %, such as in the range from 60 to 80 wt. % or in the range from 65 to 75 wt. %, based on the total weight of the lubricant.

An exemplary lubricant may be prepared from a mixture comprising one or more, such as all, of the following:
- a reactive polysiloxane
- an unreactive polysiloxane
- a catalyst
- a diluent.

An exemplary reactive polysiloxane is adapted and arranged to undergo a cross-linking reaction to obtain a cross-linked network. The cross-linking may be catalyzed by the catalyst.

An exemplary unreactive polysiloxane does not undergo a cross-linking reaction. An exemplary unreactive polysiloxane comprises one or more alkyl groups. A further exemplary unreactive polysiloxane is fully substituted with alkyl groups.

An exemplary catalyst catalyzes a reaction to cross-link polysiloxanes.

An exemplary diluent solves one or more of the other constituents of the mixture. An exemplary diluent is silicon based. An exemplary diluent is a short chain polysiloxane having 6 repeat units or less. An exemplary diluent is hexamethyl disiloxane.

An exemplary lubricant contains not more than 10 wt. % water, based on the total weight of the lubricant, such as not more than 5 wt. % or not more than 1 wt. %.

The lubricant layer has a thickness profile from p1 to p2. The thickness of the layer at p2 is greater than the thickness of the layer at p1 such as by at least 100 nm, by at least 500 nm, or by at least 1 μm.

In some embodiments, the thickness of the lubricant layer increases monotonically over the portion from p1 to p2.

In some embodiments, the thickness of the lubricant layer satisfies the following:
- the portion X is split into n sections of equal length: M1 to Mn;
- M1 to Mn are ordered, with M1 starting at p1 and Mn finishing at p2;
- the mean values T of layer thickness over the sections M1 to Mn are T1 to Tn respectively;
- each mean layer thickness T through the series T2 to Tn is greater than the preceding mean value of T: T1 to Tn−1 respectively; and
- n is an integer of 2 or more. Exemplary values for n are 5, 10, 15 and 20.

In some embodiments, the layer extends over at least 70%, such as at least 80%, at least 90%, at least 94%, at least 98%, or about 100% of the length LB of the elongate barrel section. In some embodiments, the lubricant extends over 20 to 60% of the length LB elongate barrel section.

In some embodiments, the lubricant layer has a minimum thickness tmin determined between p1 and p2 inclusive of at least 60 nm, such as at least 90 nm, at least 100 nm, or at least 110 nm.

In some embodiments, the layer has a minimum thickness tmin determined between p1 and p2 inclusive which is greater than the mean roughness of the inner surface of the side wall between p1 and p2, such as at least 20 nm greater, at least 40 nm greater, or at least 60 nm greater.

The layer of lubricant can be cured after application. Exemplary curing can be thermal or radiation induced or a combination of both. Some exemplary ways of curing are application of UV radiation and application of IR radiation.

Liquid Pharmaceutical Composition

The receptacle is for pharmaceutical packaging. An exemplary receptacle is adapted and arranged to contain a liquid. A liquid pharmaceutical composition may comprise an active compound. A liquid pharmaceutical composition is a fluid.

An exemplary amount of liquid pharmaceutical composition is in the range from 0.1 to 150 ml, such as in the range from 0.5 to 70 ml, in the range from 0.8 to 40 ml, in the range from 1 to 10 ml, or in the range from 2 to 5 ml.

Charge

The receptacle is adapted and arranged to accommodate a charge. An exemplary charge is adapted and arranged to be accommodated in the receptacle. The receptacle may be complementary such that the charge can be introduced into the interior of the receptacle and such that the charge can move within the interior in a direction parallel to the axis.

An exemplary charge is made of an elastic material or comprises a part made of an elastic material. The charge may be adapted and arranged to seal a cross-section of the interior. The charge may be adapted and arranged to move inside the receptacle, such as along the axis defined by the elongate extension of the receptacle. When inside the receptacle, movement of the charge may be resisted by a frictional force between the charge and an inside surface of the receptacle.

The charge may be attached to an elongate rod adapted and arranged to push or pull the charge in a direction parallel to the axis.

One exemplary charge is a plunger.

Charge Axial Position

When in position in the receptacle, the charge makes contact with the layer or the inner surface or both. The front end of the charge is the point of forwardmost contact, in a direction from pA to pB, of the charge with the layer or the inner surface. The back end of the charge is the point of backmost contact, in a direction from pA to pB, of the charge with the layer or the inner surface. The charge axial position is the axial position of the front end of the charge.

The distance between the front end and the back end of the charge is the charge length LC.

Kit

In some embodiments, a kit comprising a receptacle according to this disclosure and a charge according to this disclosure is provided.

The charge and the receptacle may be complementary such that the charge can be accommodated in the receptacle and can move within the interior in a direction parallel to the axis.

Frictional Forces

The movement of the charge within the receptacle is accompanied by a frictional force between the charge and the inner surface of the side wall and or the layer. The frictional force comprises both a stiction which resists the setting in motion of the charge relative to the receptacle and a dynamic friction which acts whilst the charge is in movement.

The stiction is dependent on the charge axial position. The stiction at a given charge axial position p may be determined by starting the charge at charge axial position p1+LC, moving the charge from p1+LC at a constant speed of 100 mm/minute, letting the charge come to rest at charge axial position p, for example equidistant between p1+LC and p2, and finally bringing the charge into motion in a direction to towards charge axial position p2. The stiction at charge axial position p is the force required to bring the charge into motion in the final step.

The stiction may be lower towards the second end of the receptacle than towards the first end of the receptacle, as previously described. The stiction at charge axial position p2 may be less than the stiction at charge axial position p1+LC. The stiction s may reduce monotonically from p1+LC to p2. A method for determining the stiction is presented in the figures.

The stiction may be relatively uniform from p1+LC to p2, such as satisfying the previously described criterion.

Assembly

In some embodiments, an assembly comprising a receptacle, a charge and a liquid pharmaceutical composition is provided. The charge is positioned inside the receptacle to seal a cross-section of the interior. The liquid pharmaceutical composition is present in the interior between the cross-section sealed by the charge and an aperture of the receptacle.

In some embodiments, the liquid pharmaceutical composition fills at least 50 vol. % of the interior, such as at least 70 vol. % or at least 80 vol. %.

In some embodiments, the liquid pharmaceutical composition fills less than 50 vol. % of the interior, or less than 30 vol. %, or less than 20 vol. %.

The assembly may be adapted and arranged such that the liquid pharmaceutical composition can be ejected from the interior by moving the charge in a direction parallel to the axis towards the second end.

An exemplary assembly functions as a plunger system in which the liquid pharmaceutical composition can be ejected from the receptacle through movement of the charge.

An exemplary receptacle has an attachment element, which may be at an end. An exemplary attachment element is adapted and arranged for attaching a needle or tube. A needle or tube may be attached to the receptacle in the assembly.

Luer Fitting

Exemplary receptacles, be they receptacles as such or as part of a kit or an assembly, have a Luer fitting. An exemplary Luer fitting is compatible with ISO 80369. Exemplary Luer fittings are Luer lock fittings and slip tip fittings, such as Luer lock fittings. In some embodiments, the receptacle has a Luer lock fitting. In some embodiments, the receptacle has a slip tip fitting.

An exemplary Luer fitting is a male Luer fitting. Exemplary Luer lock fittings are one-piece Luer lock fittings and two-piece Luer lock fittings. In some embodiments, the receptacle has a one-piece Luer lock fitting. In some embodiments, the receptacle has a two-piece Luer lock fitting.

Process for Preparation

A receptacle provided according to the present invention may be prepared by providing a receptacle without a lubricant layer and applying a layer of lubricant to the inner surface of the side wall of the receptacle. Exemplary methods for applying the layer are spreading and wiping, such as with a suitable tool.

An assembly may be prepared by the following steps:
providing a receptacle according to this disclosure;
introducing a charge into the receptacle, such as via a first end and via a first aperture;
introducing a liquid pharmaceutical composition into the interior of the receptacle, such as via a second end and via a second aperture.

Referring now to the drawings, FIG. 1 shows a cross-sectional view of a receptacle 100 with a lubricant layer 106 on an inner surface 118 of a side wall 107. The receptacle 100 has a first end 119 and a second end 120. At the first end 119 is a first aperture 102 and an outwardly protruding flange 105. At the second end 120 is a second aperture 103 and an attachment element 104, in this case a screw thread, for attaching a needle fitting. The receptacle 100 has an elongate barrel section 501 extending from an axial position pA to an axial position pB. As illustrated in FIG. 1, pA is closer to the first end 119 than pB and pB is closer to the second end 120 than pA. In this case, the elongate barrel section 501 has a hollow truncated conical shape with a greater diameter at pA than at pB. The length of the elongate barrel section 501 is LB. The axis 101 is in the direction of elongate extension of the receptacle 100 and is the axis of rotation of the elongate barrel section 501. The side wall 107 has an inner surface 118, on which is present a layer 106 of lubricant. The layer 106 extends over some, but not all of the side wall 107, not reaching the ends pA and pB. A portion X of the elongate barrel section 501 runs between axial positions p1, which is closer to pA (and the first end 119) than pB (and the second end 120), to p2, which is closer to pB (and the second end 120) than pA (and the first end 119). The portion X is an abstract portion selected according to the criteria described herein. The end points p1 and p2 both lie within the bounds of the layer 106. The purpose of selecting the abstract portion X of the elongate barrel section 501 is to ensure that irregularities at the ends of the elongate barrel section 501 are avoided, in particular since the layer 106 may not extend all the way to the ends pA and pB, as in this example. Axial positions along the receptacle 100 are measured along the axis 101. Axial positions may be given with reference to p1 as a fiduciary zero point. Shown is a general axial position p as well as the internal diameter 118 between of the inner surfaces 118 of the side walls 107 at that axial position. The thicknesses t1 at axial position p1 and t2 at axial position p2 are shown. According to the present invention, t2 is greater than t1. In the case shown, t1 and t2 are rather similar, but the difference could be much more marked.

FIGS. 2A to 2M show a multi-push movement of a charge 203 in a receptacle 100. The series of figures demonstrates how the charge 203 may be pushed along the axis 101 of the receptacle 100 in multiple pushes in between which the charge 203 comes to rest at least once on its path along the axis 101. In the process shown, the charge 203 comes to rest at two intermediate axial positions along its path. The process presented can also be used to construct a profile of dynamic friction and stiction for the receptacle/charge combination as a function of distance along the axis 101. The process is performed using a TesT 106.2 kN device commercially available from TesT GmbH, Germany.

Figure 2A:
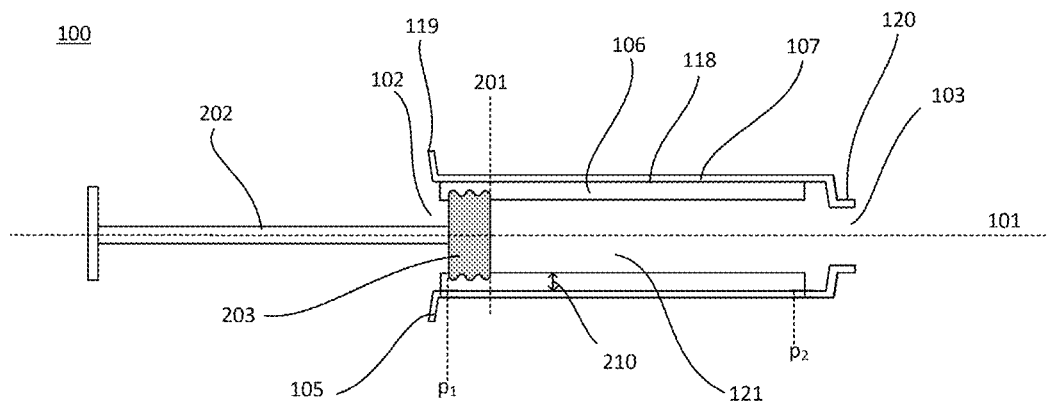
FIGS. 2A to 2M illustrate a multi-push movement of a charge in a receptacle.

FIG. 2A shows a receptacle 100 ready for multi-push movement of a charge 203. The receptacle 100 is in this case a syringe barrel, having a major hollow truncated conical section (The angle of inclination of the truncated cone is very slight and the elongate barrel section has been represented as a cylinder for simplicity of view). An axis 101 is in the direction of the elongate extension of the receptacle 100. The axis 101 is the axis of rotation of the conical/cylindrical section. At a first end 119 of the receptacle 100 is a first aperture 102 and an outwardly protruding flange 105. At a second end 120 of the receptacle is a second aperture 103 which exhibits a narrowing and is adapted and arranged to attach a needle. The first aperture 102 has a greater diameter area than the second aperture 103. The receptacle 100 has a cylindrical side wall 107 and an interior 121. A layer 106 of lubricant is present on the inner surface 118 of the side wall 107. The lubricant layer 106 is present along the majority of the side wall 107. In this case, the portion X covers most of the lubricant layer 107, with p1 and p2 slightly removed from the ends of the layer 107 in order to avoid end effects. The layer 106 of lubricant has a thickness 210, shown at a general axial position along the axis 101. For ease of depiction, the layer 106 is shown roughly uniform, but exemplary thickness profiles are described elsewhere herein. Present in the interior 121, towards the first end 119 of the receptacle 100, is a charge 203. In this case, the charge 203 is a stopper of elastomer material having an attached elongate rod 202. The charge 203 has ribbed side walls. The elongate rod 202 can be used to push the charge 203 along the axis 101 in the manner of a plunger. The axial position of the charge 203 is defined as the axial position of the front end of the charge 203. The charge 203 is shown in an initial axial position 201 in which the back end of the charge 203 is at p1. In the initial state presented, no force is applied to the charge via the elongate rod 202 and the charge 203 is at rest.

Figure 2B:
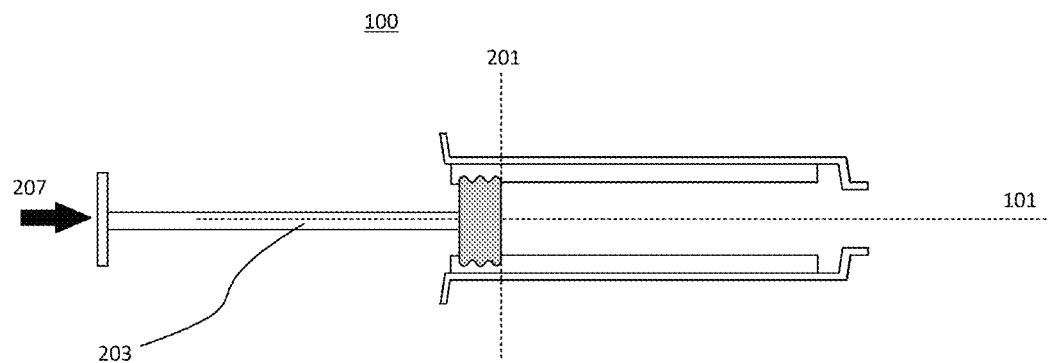

FIG. 2B shows the receptacle 100 of FIG. 1, in which a pushing force 207 is applied to the elongate rod 202 in a direction along the axis 101. The force 207 is transferred to the charge 203. In the figure, the force 207 is inferior to the stiction at the axial position 201 and the charge 203 is at rest, with the pushing force 207 cancelled out by the static frictional force between the charge 203 and the side walls 207/lubricant layer 106. The stiction at the axial position 201 is determined as the force 207 at which the charge 203 starts to move along the axis 101.

Figure 2C:
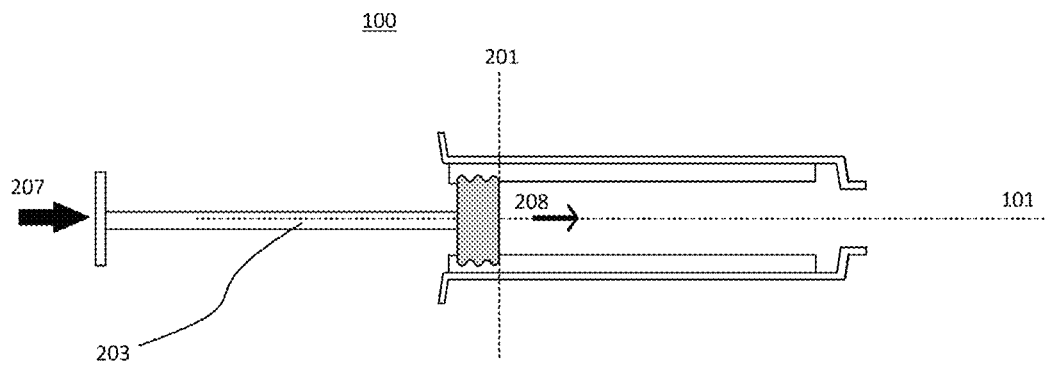

FIG. 2C shows the receptacle 100 immediately after the pushing force 207 in FIG. 2B exceeds the stiction at axial position 201 to put the charge 203 into motion. The charge 203 is depicted at the axial position 201, but in motion 208 along the axis 101. The pushing force 207 is equal to the dynamic friction at axial position 201 and the charge 203 is in a state of constant velocity along the axis 101. The charge 203 is moved between rest axial positions at a constant speed of 100 mm/min.

Figure 2D:
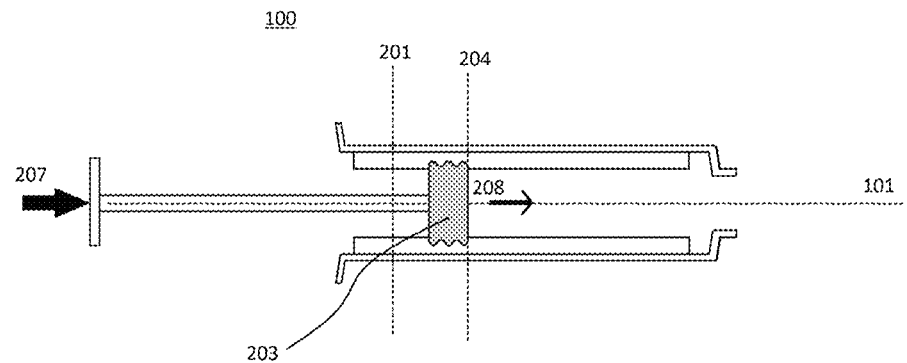

FIG. 2D shows the receptacle 100 subsequent to that of FIG. 2C, in which the charge 203 has travelled a distance from 201 to an intermediate axial position 204 along the axis 101. The charge 203 is still in motion 208 with constant velocity of 100 mm/min with the pushing force 207.

Figure 2E:
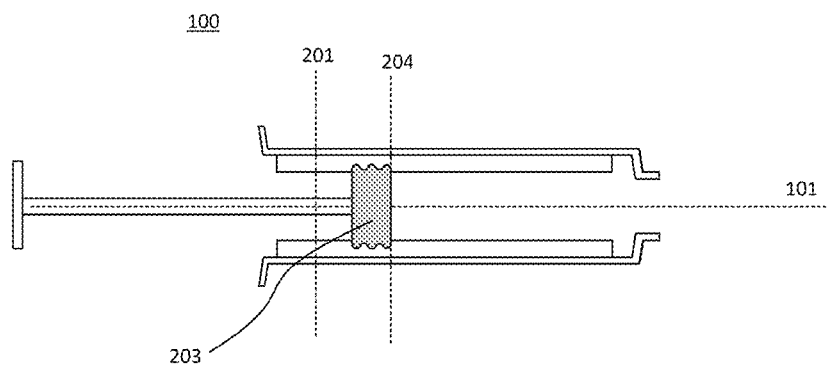

FIG. 2E shows the receptacle 100 in which the pushing force 207 has been released at axial position 204. The charge is at rest at the axial position 204.

Figure 2F:
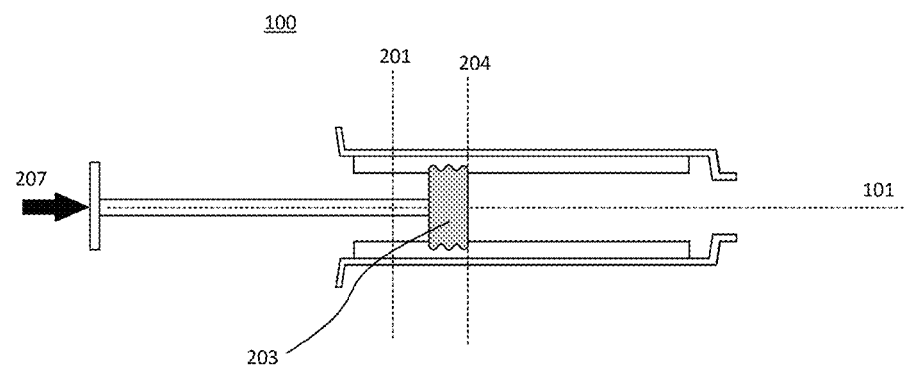
Figure 2G:
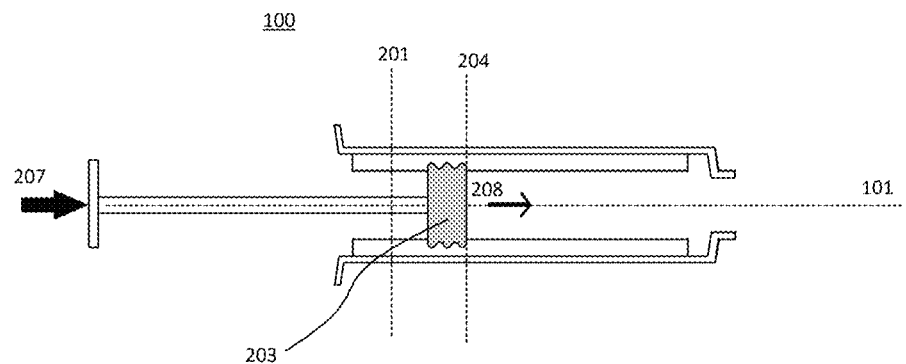
Figure 2H:
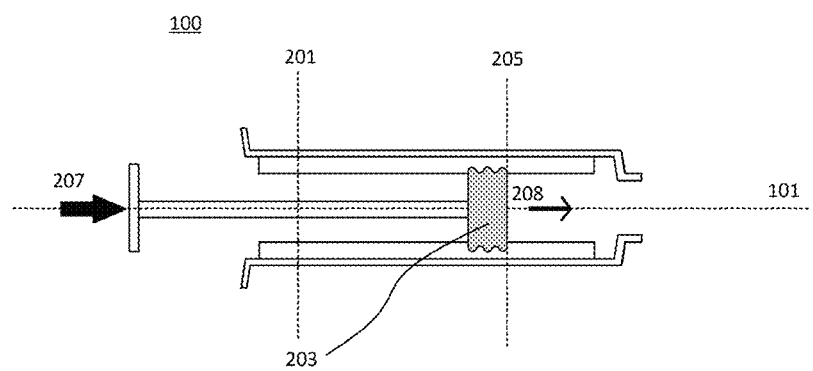
Figure 2I:
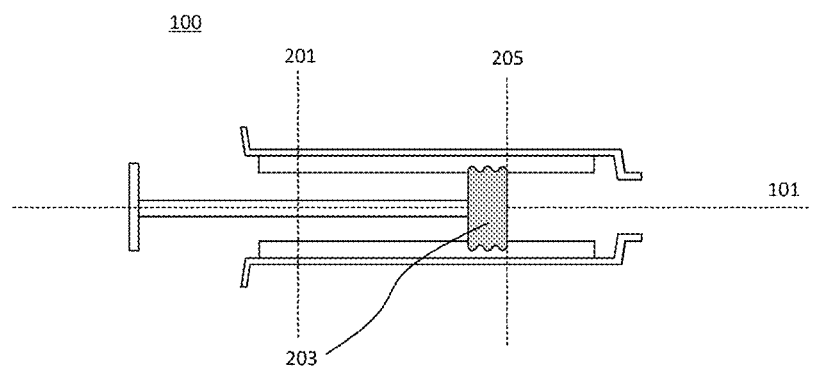

FIGS. 2E to 2I are analogous to FIGS. 2A to 2E. The charge 203 is initially at rest at axial position 204 (FIG. 2E) and is set in motion 208 by a force 207 exceeding the stiction at axial position 204 (FIG. 2F). The charge 203 starts moving 208 along the axis 101 at axial position 204 (FIG. 2G) and arrives in motion 208 at a further intermediate axial position 205 (FIG. 2H), where the pushing force 207 is released and the charge 203 comes to a stop (FIG. 2I).

The speed between rest axial positions is maintained constant at 100 mm/min.

Figure 2J:
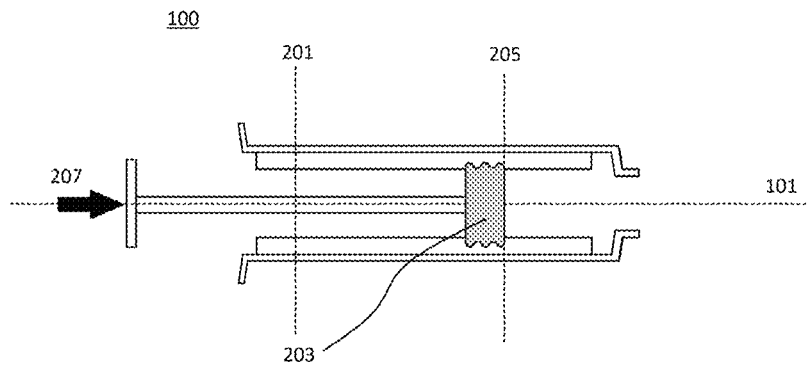
Figure 2K:
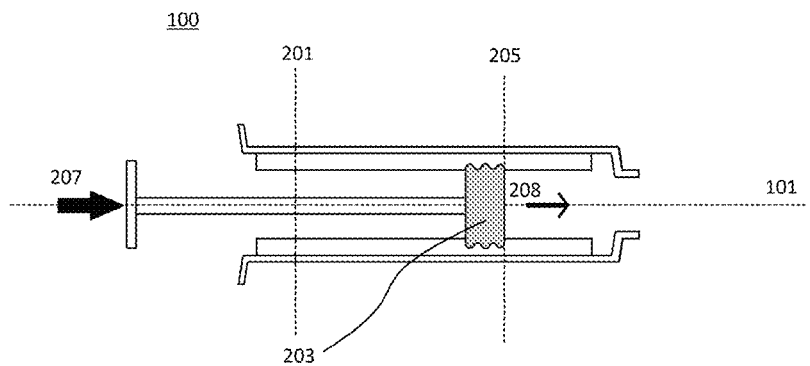
Figure 2L:
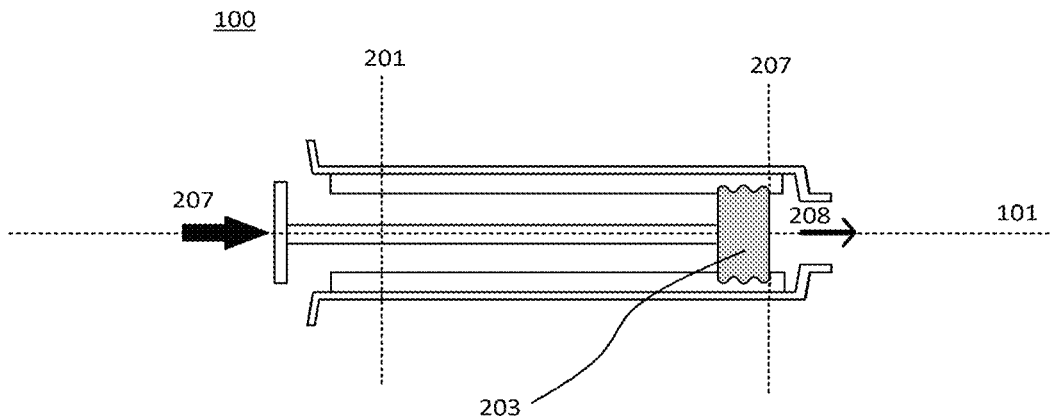
Figure 2M:
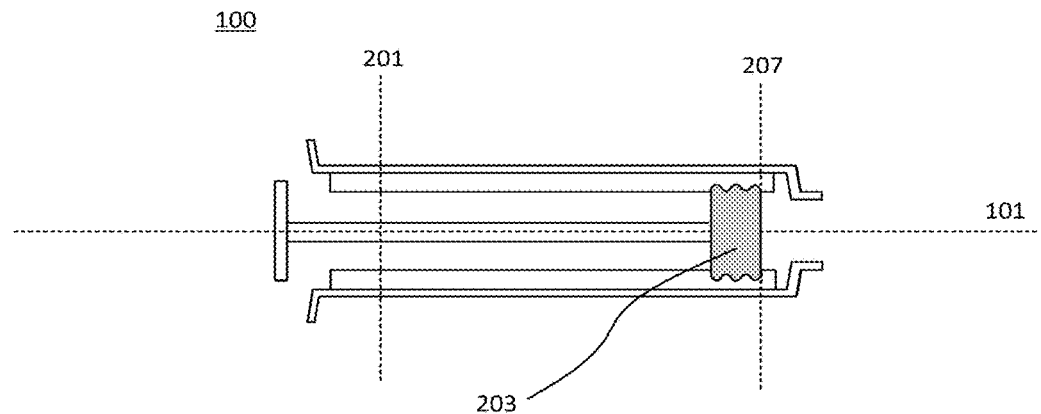

FIGS. 2I to 2M are analogous to FIGS. 2A to 2E and FIGS. 2E to 2I respectively. The charge 203 is initially at rest at axial position 205 (FIG. 2I) and is set in motion 208 by a force 207 exceeding the stiction at axial position 205 (FIG. 2J). The charge 203 starts moving 208 along the axis 101 at axial position 205 (FIG. 2K) and arrives in motion 208 at the final axial position 206 (FIG. 2L), where the pushing force 207 is released and the charge 203 comes to a stop (FIG. 2M). The axial position 206, is where the front end of the charge has arrived at axial position p2, close to the end of the lubricated layer 106 and is in its final rest axial position. The speed between rest axial positions is maintained constant at 100 mm/min.

The stiction at points 201, 204 and 205 are measured at the following points:

| 201 | FIG. 2B |
| 204 | FIG. 2F |
| 205 | FIG. 2J |

Figure 3:
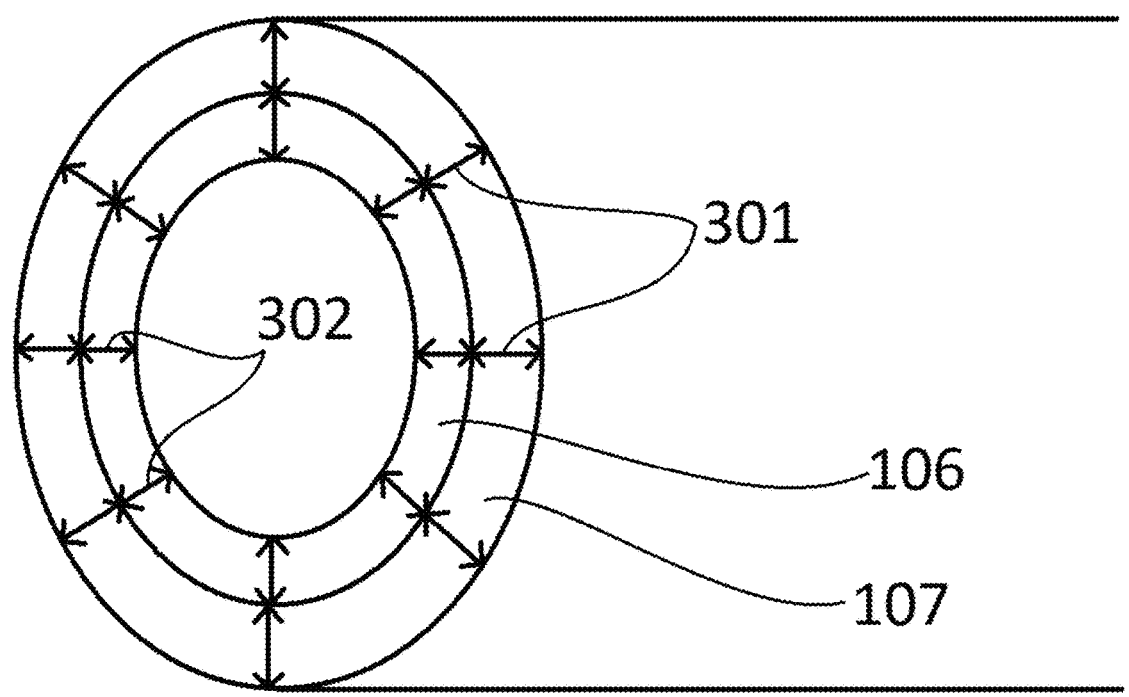
FIG. 3 illustrates a cross-sectional view through the receptacle.

FIG. 3 shows a cross-sectional view through the receptacle 100 at an axial position p along the axis 101. The side wall 107 and the lubricant layer 106 are shown as concentric circular bands. The thickness 301 of the side wall 107 and the thickness 302 of the lubricant layer 106 are each shown at 8 equidistant points around the circle. A thickness of a side wall 107 or a layer 106 of lubricant at an axial position p is a mean of the thickness around the circle. This is measured as the mean of a number of equally spaced sample points around the circle, in this case 8.

FIGS. 4A to 4E show the process of preparing an assembly and ejecting a pharmaceutical product 401.

Figure 4A:
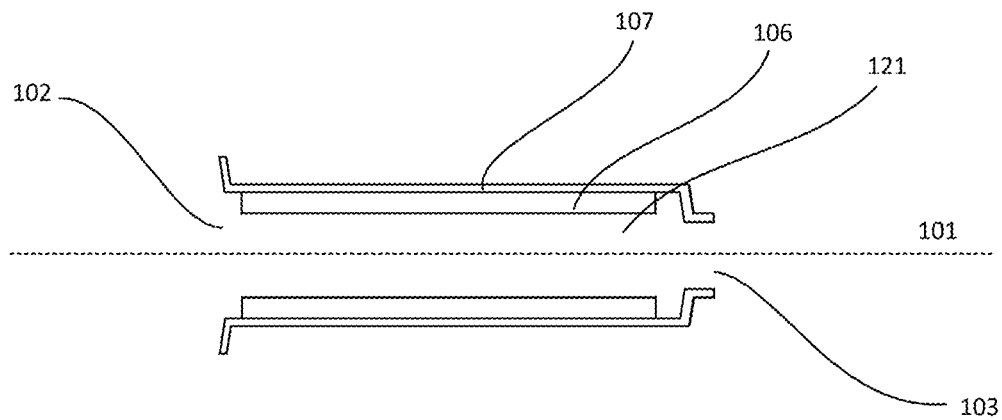
FIGS. 4A to 4E illustrate a process of preparing an assembly and ejecting a pharmaceutical product.
Figure 4B:
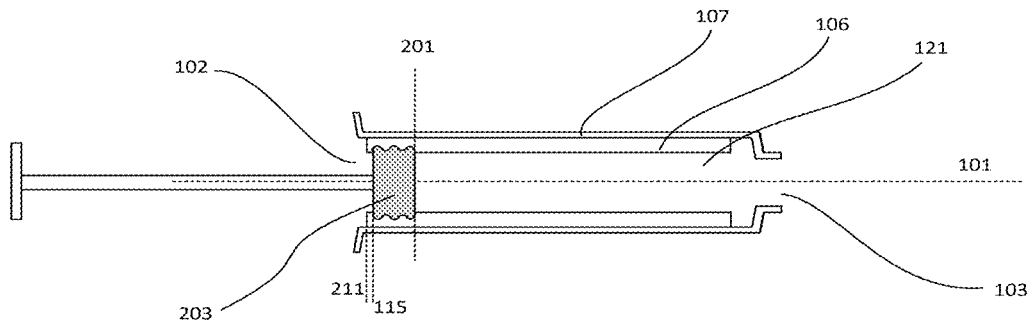

FIG. 4A shows a receptacle 100, ready for forming an assembly. The receptacle 100 has an axis of rotation 101, a side wall 107 and an interior 121. A layer 106 of lubricant is present on the inside of the receptacle 100. The layer 106 of lubricant has been cured by heating at 175° C. for 20 seconds. The receptacle 100 has a first aperture 102 and a second aperture FIG. 4B shows the receptacle 100 of FIG. 4A with a charge 203 located in the interior 121. The front end of the charge 203 is at an axial position 201 along the axis, close to the first aperture 102. The back end of the charge 203 is at p1, close to the start of the lubricant layer 107.

Figure 4C:
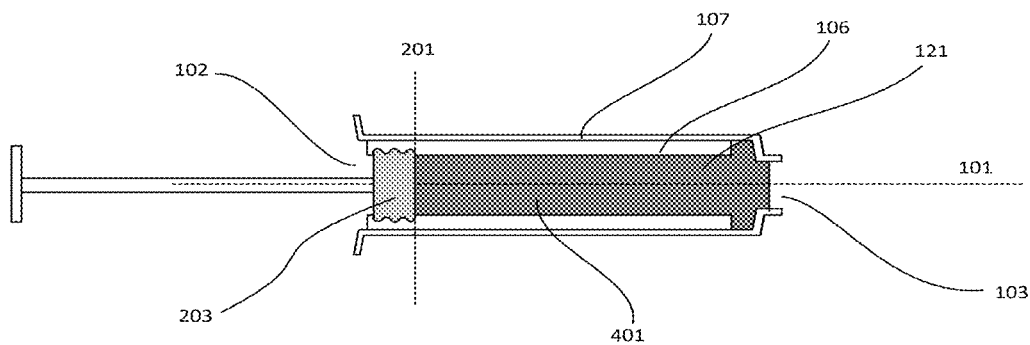

FIG. 4C shows the receptacle 100 of FIG. 4B after having been filled with a liquid pharmaceutical composition 401. The liquid pharmaceutical composition 401 is located in the interior 121 between the front end of the charge 201 and the second aperture 103. In this form, the receptacle 100, the charge 203 and the liquid pharmaceutical composition 401 constitute an assembly.

Figure 4D:
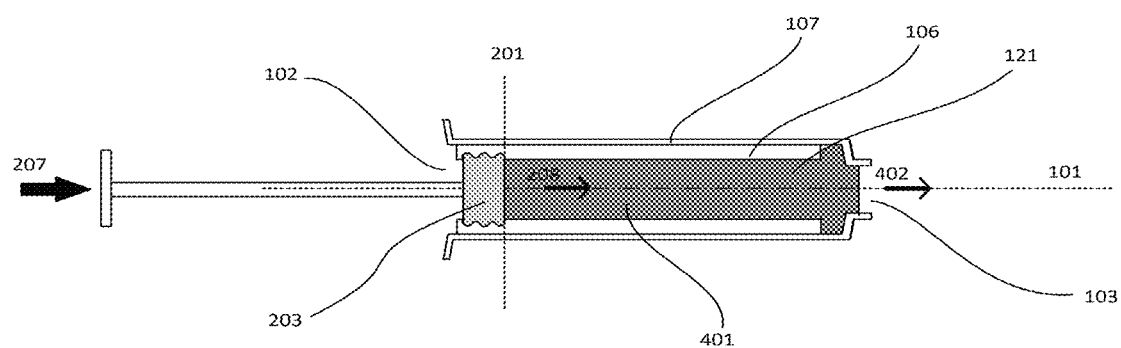

FIG. 4D shows the assembly of FIG. 4C in which a pushing force 207 is applied to push the charge 203 along the axis 101 in a direction from the first aperture 102 towards the second aperture 103. The motion 208 of the charge 203 forces the liquid pharmaceutical composition 401 to be ejected 402 from the receptacle 100.

Figure 4E:
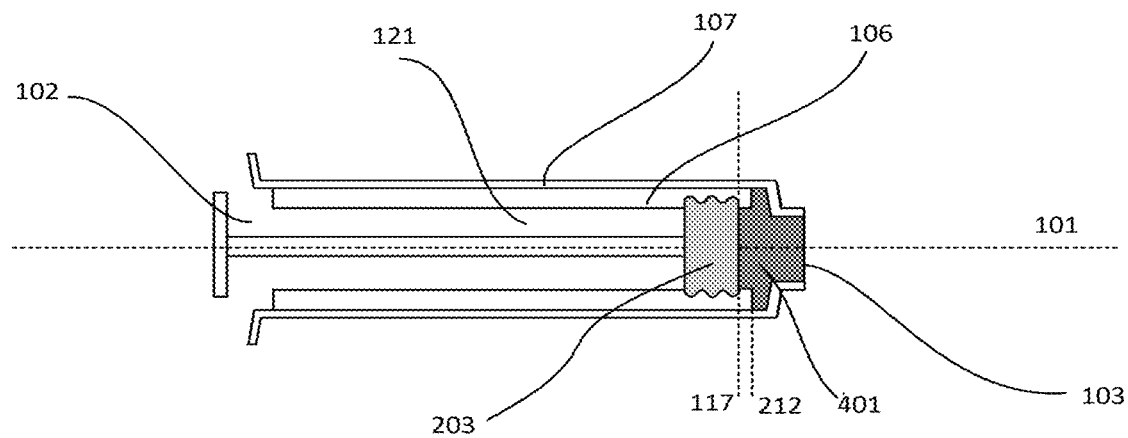

FIG. 4E shows the assembly of FIG. 4D once the charge 203 has travelled along the axis 101 in a direction from the first aperture 102 towards the second aperture 103 to arrive at axial position p2 near the end of the layer 106 of lubricant. The liquid pharmaceutical composition 401 has been ejected via the second aperture 103 and only a small quantity remains in the tip of the receptacle at the second aperture 103.

Figure 5:
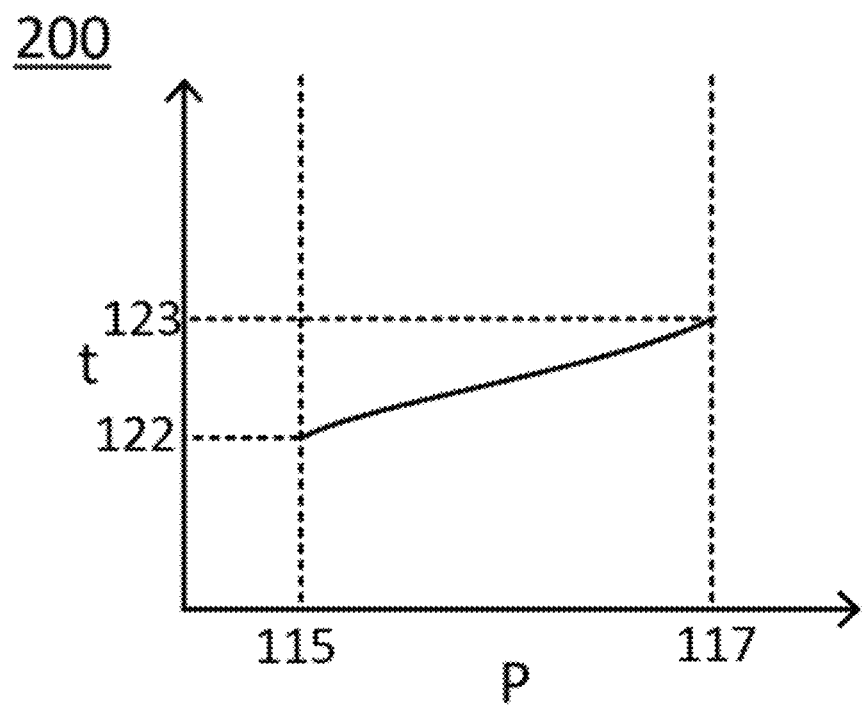
FIG. 5 illustrates a thickness profile of the layer of lubricant.

FIG. 5 shows a thickness profile 200 of the layer 106 of lubricant. The thickness t increases from a value of t1 122 at an axial position p1 115 to a value of t2 123 at an axial position p2 117. The gradient of the thickness against axial position is not negative anywhere along the extent from p1 115 to p2 117. The profile is monotonic.

Figure 6:
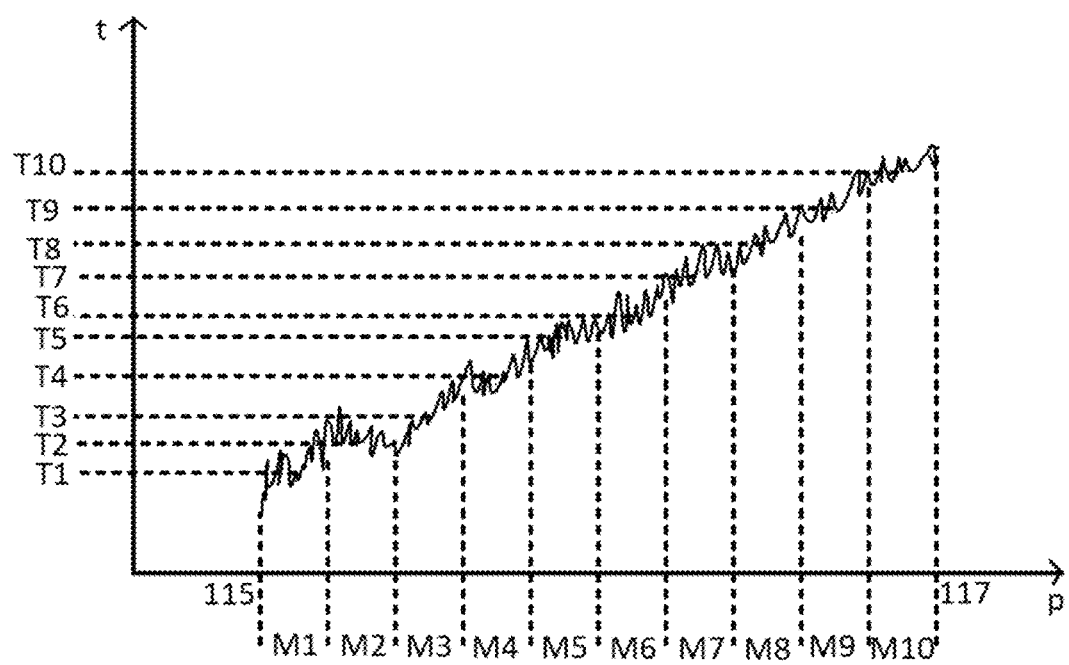
FIG. 6 illustrates determination of a monotonically increasing thickness profile.

FIG. 6 shows determination of a monotonically increasing thickness profile. The stretch from p1 to p2 has been split into 10 sections M1 to M10 of equal size. The mean thickness over the sections M1 to M10 is T1 to T10 respectively. Despite sharp variations of the thickness profile on a short range due to roughness, the longer-range monotonicity of the thickness profile is evident from the strictly ascending ordering from T1 to T10, without descending, as can be seen on the t axis.

Figure 7:
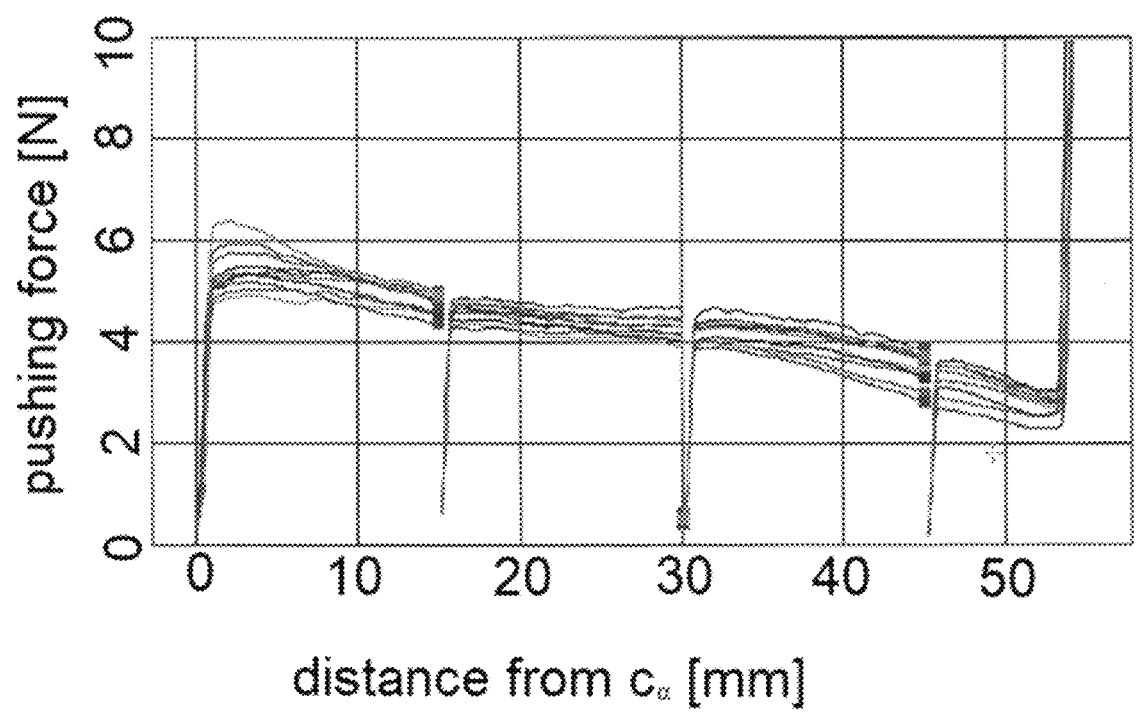
FIG. 7 illustrates a stiction profile for an exemplary embodiment of a kit provided according to the present invention.

FIG. 7 shows a stiction profile for an exemplary embodiment of a kit provided according to the present invention.

The stiction profile is determined using the procedure as presented in t FIGS. 2A to 2M, except with 3 intermediate rest points at 15, 30 and 45 mm from the start point 201. The test was performed 10 times with fresh kits (all 10 lines shown in the figure). In each run, a smooth stiction profile was observed, mildly decreasing from around 4.8-6.2 N at 201 to around 2.8-3.8 N at 45 mm from ca. The gently and monotonically decreasing stiction profile is well suited to be employed in a multi-dose syringe. As can be seen, the transition between stiction and dynamic friction is smooth, allowing better control of multi-dose ejection.

Test Methods

Layer Thickness

The thickness of the layer is determined by optical interference measurements using the RapID Explorer available from rap.ID Particle Systems GmbH. Measurements are taken from outside the receptacle through the side wall. The device is operated with the proprietary software and in accordance with the 2014 proprietary instruction manual.

Surface Roughness

Surface roughness of the inner surface of the side wall is measured using a white-light interference microscope. An area of the sample of 2 µm by 2 µm is scanned in tapping mode, scanning the area with 256 lines per picture and 256 dots per line. The scan rate is 0.7 Hz. The cantilever has a tip with a tip radius of ≤10 nm. The sample's topography is measured by evaluating the change of the amplitude of the oscillating cantilever when scanning the surface. The raw data is levelled by a line fit, using a $3^{rd}$ order polynomial fit. The root mean squared roughness Rrms is calculated by the AFM's software using the formula $$R_{rms} = \sqrt{\frac{1}{n}\sum_{i=1}^{n} y_i^2},$$

where n=256*256=65536 and yi is the height value at each of the 65536 measured positions.

Resistive Force

Resistive force is measured using a TesT 106.2 kN device commercially available from TesT GmbH, Germany. The charge is moved with a speed of 100 mm/minute.

Examples

The following examples are for further elucidation of the invention and do not limit the scope of the claimed invention.

A lubricant was prepared as follows: 10 g of a vinyl-functionalized polydimethylsiloxane were initially charged in a reaction vessel and admixed with 65 g of decamethylcyclopentasiloxane. Under constant stirring at 800 rpm, 0.5 g of methylhydrosiloxane/dimethylsiloxane copolymer, 6.25 g of liquid polydimethylsiloxane, 0.01 g of 10% hexachloroplatinic acid in isopropanol as catalyst and 0.05 g of 2,4,7,9-tetramethyl-5-decyne-4,7-diol as inhibitor were added to this reaction mixture. The reaction solution was used after a stirring time of 60 s. A receptacle was provided according to FIG. 1. The receptacles was a 1 ml 1 g TopPac available from Schott AG Germany. The inner surface of the side walls of the elongate barrel section was coated with a coating of the lubricant, extending up to 1 mm from each of the two ends of the elongate barrel section. The thickness profile of the applied layer was according to Examples 1-4 of Table 1. The lubricant layer was cured by heating at 175° C. for 20 seconds. The receptacle was tested by introducing a charge made of elastomer with an attached elongate rod according to FIG. 2A, charge FM 257/2 available from Dedecke GmbH, Germany. The process similar to that displayed in FIGS. 2A to 2M, starting at 5 mm along the barrel and with 3 intermediate stop points, at 15, 30 and 45 mm along the barrel, was performed to determine the stiction along the barrel for Examples 1-4, with the stiction values being presented in Table 2. The process is performed using a TesT 106.2 kN device commercially available from TesT GmbH, Germany.

The root mean square of the roughness of the inner surface of the side wall over the section from p1 to p2 was determined to be 62 nm.

TABLE 1

| Example | Distance along barrel [mm] | | | | | | |
|---|---|---|---|---|---|---|---|
| | 0 | 10 | 20 | 30 | 40 | 50 | 60 |
| | Thickness t [nm] | | | | | | |
| 1 | 71 | 279 | 722 | 1014 | 1304 | 1708 | 1863 |
| 2 | 74 | 511 | 1423 | 1982 | 2356 | 2870 | 3987 |
| 3 | 2102 | 1677 | 1298 | 1012 | 697 | 311 | 69 |
| 4 | 956 | 944 | 963 | 961 | 948 | 951 | 960 |

TABLE 2

| Example | Distance along barrel [mm] | | | |
|---|---|---|---|---|
| | 5 | 15 | 30 | 45 |
| | Stiction [N] | | | |
| 1 | 6.2 | 5.0 | 4.3 | 3.7 |
| 2 | 5.7 | 4.6 | 3.8 | 2.8 |
| 3 | 5.8 | 6.4 | 7.1 | 7.8 |
| 4 | 6.0 | 6.1 | 6.1 | 6.2 |

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

REFERENCE LIST

100 Receptacle
101 Axis
102 First aperture
103 Second aperture
104 Attachment element at front end of receptacle
105 Outwardly protruding flange of receptacle
106 Layer of lubricant
107 Side wall of receptacle
118 Inner surface of side wall
119 First end of receptacle
120 Second end of receptacle
121 Interior of receptacle
201 Initial charge axial position
202 Elongate rod for pushing charge
203 Charge
204 First intermediate charge axial position
205 Second intermediate charge axial position
206 Final charge axial position 207 Pushing force
208 Movement of charge along axis
210 Thickness of layer at a general axial position
301 Thicknesses of the side wall
302 Thicknesses of the layer
401 Liquid pharmaceutical composition
402 Ejection of liquid pharmaceutical composition
501 Elongate barrel section

What is claimed is:

1. A receptacle for pharmaceutical packaging, comprising:
an elongate barrel section, the elongate barrel section having a direction of elongate extension and an axis in the direction of elongate extension, an axial position p is determined along the axis, the elongate barrel section extends from an axial position pA to an axial position pB, wherein pA is a first axial terminal end position of the elongate barrel section and pB is a second axial terminal end position of the elongate barrel section that is opposite the first axial terminal end position and an elongate barrel section length LB is a distance between pA and pB;
a side wall extending over the elongate barrel section, the side wall having an inner surface bordering an interior, the interior having a diameter; and
a layer of a lubricant located on at least a part of the inner surface; at a given axial position p on the axis between pA and pB, a thickness of the side wall, a thickness of the layer, and the diameter of the interior are each determined as an angular mean in a cross-sectional plane perpendicular to the axis at the axial position p;
a portion X of the axis extends from an axial position p1 to an axial position p2 such that the following criteria are satisfied:
i. both p1 and p2 lie between pA and pB,
ii. a portion length LX is a distance between p1 and p2,
iii. LX is at least 60% of the length LB,
iv. the layer extends over the entire portion X, and
v. a thickness t1 of the layer at the axial position p1 is less than a thickness t2 of the layer at the axial position p2, wherein the thickness of the layer increases monotonically over the entire portion X from p1 to p2;
wherein at least one criteria is satisfied and is selected from the group consisting of:
the length LB is in a range from 3 cm to 20 cm;
a mean value of the diameter of the interior determined over a range pA to pB is in a range from 0.4 cm to 4 cm;
a mean thickness of the sidewall determined over the range pA to pB is in a range from 0.3 mm to 4 mm; and
a volume of the interior is in a range from 0.1 ml to 150 ml.

2. The receptacle of claim 1, wherein a ratio of the thicknesses t1:t2 is in a range from 1:1.1 to 1:100.

3. The receptacle of claim 2, wherein the ratio of the thicknesses t1:t2 is in a range from 1:15 to 1:70.

4. The receptacle of claim 1, wherein the lubricant comprises one or more silicone oils.

5. The receptacle of claim 4, wherein the one or more silicone oils are at least partially contained in a matrix.

6. The receptacle of claim 1, wherein the interior is cylindrical or truncated conical over the elongate barrel section.

7. The receptacle of claim 1, further comprising a first aperture at a first end and a second aperture at a second end.

8. The receptacle of claim 1, wherein the diameter of the interior at p1 is d1 and the diameter of the interior at p2 is d2 and d1 is greater than d2.

9. The receptacle of claim 1, further comprising an aperture and an attachment element at the aperture.

10. The receptacle of claim 1, wherein the layer has a minimum thickness tmin determined in the portion X of at least 60 nm.

11. The receptacle of claim 1, wherein the thickness t2 of the layer at p2 is at least 100 nm greater than the thickness t1 of the layer at p1.

12. The receptacle of claim 1, wherein the layer has a minimum thickness tmin determined between p1 and p2 inclusive that is greater than a mean roughness of the inner surface of the side wall between p1 and p2.

13. The receptacle of claim 1, wherein the portion X is split into n sections of equal length $M_1$ to $M_n$; the sections $M_1$ to $M_n$ are ordered, with section $M_1$ starting at $p_1$ and section $M_n$ finishing at p2; mean values of layer thickness over the sections $M_1$ to $M_n$ are $T_1$ to $T_n$ respectively; each mean layer thickness T through the series $T_2$ to $T_n$ is greater than the preceding mean value of T:$T_1$ to $T_{n-1}$ respectively; and n is an integer of 2 or more.

14. The receptacle of claim 1, wherein LX is at least 80% of the length LB.

15. A kit, comprising:
a receptacle, the receptacle comprising:
an elongate barrel section, the elongate barrel section having a direction of elongate extension and an axis in the direction of elongate extension, an axial position p is determined along the axis, the elongate barrel section extends from an axial position pA to an axial position pB, wherein pA is a first axial terminal end position of the elongate barrel section and pB is a second axial terminal end position of the elongate barrel section that is opposite the first axial terminal end position and an elongate barrel section length LB is a distance between pA and pB;
a side wall extending over the elongate barrel section, the side wall having an inner surface bordering an interior, the interior having a diameter; and
a layer of a lubricant located on at least a part of the inner surface; at a given axial position p on the axis between pA and pB, a thickness of the side wall, a thickness of the layer, and the diameter of the interior are each determined as an angular mean in a cross-sectional plane perpendicular to the axis at the axial position p; a portion X of the axis extends from an axial position p1 to an axial position p2 such that the following criteria are satisfied:
both p1 and p2 lie between pA and pB,
a portion length LX is a distance between p1 and p2,
LX is at least 60% of the length LB,
the layer extends over the entire portion X, and
a thickness t1 of the layer at p1 is less than a thickness t2 of the layer at p2, wherein the thickness of the layer increases monotonically over the entire portion X from p1 to p2;
wherein at least one criteria is satisfied and is selected from the group consisting of:
the length LB is in a range from 3 cm to 20 cm;
a mean value of the diameter of the interior determined over a range pA to pB is in a range from 0.4 cm to 4 cm;
a mean thickness of the sidewall determined over the range pA to pB is in a range from 0.3 mm to 4 mm; and a volume of the interior is in a range from 0.1 ml to 150 ml; and a charge that is adapted and arranged to be positioned in the interior such that:
  i. the charge seals a cross section of the interior between the inner surface of the side wall and another inner surface of a second side wall;
  ii. the charge has a front end at an axial position closest to pB at which the charge contacts the layer or the inner surface;
  iii the charge has a back end at an axial position closest to pA at which the charge contacts the layer or the inner surface;
  iv a length of the charge LC is a distance between the front end and the back end;
  v. the charge has a charge axial position, being the axial position of the front end; and
  vi. the charge is movable in a direction parallel to the axis with a stiction s, the stiction s being a function of the charge axial position.

16. The kit of claim 15, wherein, for charge axial positions in a range from p1+LC to p2, the stiction s has a maximum value smax, a minimum value smin and the value of smin/smax is 70% or more.

17. The kit of claim 15, wherein the stiction s at a charge axial position p2 is equal to or less than the stiction s at a charge axial position p1+LC.

18. The kit of claim 15, wherein the stiction s reduces monotonically from p1+LC to p2.

19. An assembly, comprising:
a receptacle, the receptacle comprising:
  an elongate barrel section, the elongate barrel section having a direction of elongate extension and an axis in the direction of elongate extension, an axial position p is determined along the axis, the elongate barrel section extends from an axial position pA to an axial position pB, wherein pA is a first axial terminal end position of the elongate barrel section and pB is a second axial terminal end position of the elongate barrel section that is opposite the first axial terminal end position and an elongate barrel section length LB is a distance between pA and pB;
  a side wall extending over the elongate barrel section, the side wall having an inner surface bordering an interior, the interior having a diameter; and
  a layer of a lubricant located on at least a part of the inner surface; at a given axial position p on the axis between pA and pB, a thickness of the side wall, a thickness of the layer, and the diameter of the interior are each determined as an angular mean in a cross-sectional plane perpendicular to the axis at the axial position p; a portion X of the axis extends from an axial position p1 to an axial position p2 such that the following criteria are satisfied:
  both p1 and p2 lie between pA and pB,
  a portion length LX is a distance between p1 and p2,
  LX is at least 60% of the length LB,
  the layer extends over the entire portion X, and
  a thickness t1 of the layer at p1 is less than a thickness t2 of the layer at p2, wherein the thickness of the layer increases monotonically over the entire portion X from p1 to p2;
  wherein at least one criteria is satisfied and is selected from the group consisting of:
  the length LB is in a range from 3 cm to 20 cm;
  a mean value of the diameter of the interior determined over a range pA to pB is in a range from 0.4 cm to 4 cm;
  a mean thickness of the sidewall determined over the range pA to pB is in a range from 0.3 mm to 4 mm; and
  a charge, wherein:
    a. the receptacle has an aperture;
    b. the charge is positioned in the interior sealing a cross section of the interior;
    c. the interior contains a liquid pharmaceutical composition, located between the sealed cross section and the aperture; and
    d. the assembly is adapted and arranged for the liquid pharmaceutical composition to be ejected through the aperture by movement of the charge in a direction parallel to the axis.

20. The assembly of claim 19, wherein the charge is movable in a direction parallel to the axis with a stiction s, the stiction s being a function of an axial position of the charge, the charge defining a length of the charge LC that is a distance between a front end and a back end of the charge, the stiction s reducing monotonically from p1+LC to p2.

* * * * *